(12) United States Patent
Baik et al.

(10) Patent No.: US 11,401,289 B2
(45) Date of Patent: Aug. 2, 2022

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Chul Baik, Suwon-si (KR); Taejin Choi, Suwon-si (KR); Ji Soo Shin, Seoul (KR); Sung Young Yun, Suwon-si (KR); Kyung Bae Park, Hwaseong-si (KR); Gae Hwang Lee, Seongnam-si (KR); Yeong Suk Choi, Suwon-si (KR); Chul Joon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 224 days.

(21) Appl. No.: 16/910,838

(22) Filed: Jun. 24, 2020

(65) Prior Publication Data

US 2020/0407384 A1 Dec. 31, 2020

(30) Foreign Application Priority Data

Jun. 25, 2019 (KR) .................. 10-2019-0075908

(51) Int. Cl.
*C07F 11/00* (2006.01)
*C07F 7/30* (2006.01)
(Continued)

(52) U.S. Cl.
CPC ............... *C07F 11/00* (2013.01); *C07F 7/30* (2013.01); *H01L 27/307* (2013.01); *H01L 51/44* (2013.01)

(58) Field of Classification Search
CPC ................ C07F 11/00; H01L 51/0059; H01L 51/0053; H01L 51/0071; H01L 51/0074
See application file for complete search history.

(56) References Cited

U.S. PATENT DOCUMENTS

| 6,300,612 B1 | 10/2001 | Yu |
| 7,129,466 B2 | 10/2006 | Iwasaki |

(Continued)

FOREIGN PATENT DOCUMENTS

| EP | 2887413 A1 | 6/2015 |
| JP | 6145872 B2 | 6/2017 |

(Continued)

OTHER PUBLICATIONS

European Search Report dated Aug. 21, 2020, issued in corresponding European Patent Application No. 20181848.1.
(Continued)

*Primary Examiner* — Anthony Ho
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

(Continued)

In Chemical Formula 1, the definition of each substituent is as described in the detailed description.

18 Claims, 9 Drawing Sheets

(51) Int. Cl.
*H01L 27/30* (2006.01)
*H01L 51/44* (2006.01)

(56) References Cited

U.S. PATENT DOCUMENTS

| | | | |
|---|---|---|---|
| 7,973,307 | B2 | 7/2011 | Rand et al. |
| 8,035,708 | B2 | 10/2011 | Takizawa et al. |
| 8,426,727 | B2 | 4/2013 | Pfeiffer et al. |
| 8,525,577 | B2 | 9/2013 | Yofu et al. |
| 8,890,134 | B2 | 11/2014 | Lee et al. |
| 9,911,920 | B2 | 3/2018 | Bulliard et al. |
| 2007/0012955 | A1 | 1/2007 | Ihama |
| 2012/0313088 | A1 | 12/2012 | Yofu et al. |
| 2016/0020401 | A1 | 1/2016 | Bulliard et al. |
| 2018/0006090 | A1 | 1/2018 | Leem et al. |
| 2019/0043926 | A1 | 2/2019 | Yamada et al. |
| 2019/0092743 | A1 | 3/2019 | Nishide et al. |
| 2019/0389832 | A1 | 12/2019 | Morse et al. |
| 2020/0052216 | A1 | 2/2020 | Mitchell et al. |
| 2020/0052227 | A1 | 2/2020 | Morse et al. |
| 2020/0066998 | A1 | 2/2020 | Morse et al. |

FOREIGN PATENT DOCUMENTS

| | | |
|---|---|---|
| JP | 2017214353 A | 12/2017 |
| JP | 2018020976 A | 2/2018 |
| KR | 101099601 B1 | 12/2011 |
| KR | 101374377 B1 | 3/2014 |
| KR | 20160011039 A | 1/2016 |
| KR | 20180002272 A | 1/2018 |
| KR | 101860084 B1 | 5/2018 |
| WO | WO-2014026244 A1 | 2/2014 |
| WO | WO-2018007479 A1 | 1/2018 |
| WO | WO-2018065356 A1 | 4/2018 |

OTHER PUBLICATIONS

H. Seo et al., 'Color Sensors with Three Vertically Stacked Organic Photodetectors' *Japanese Journal of Applied Physics*, vol. 46, No. 49, 2007, pp. L1240-L1242.

S. Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

M. Ihama et al., 'CMOS Image Sensor with a Thin Overlaid Panchromatic Organic Photoconductive Layer for Sensors with Reduced Pixel Size' *IDW*, 2009, pp. 2123-2126.

R. Hecht et al., 'n-Channel Organic Semiconductors Derived from Air-Stable Four-Coordinate Boron Complexes of Substituted Thienylthiazoles' *Chemistry: A European Journal*, 2017, 10.1002/chem.201701922.

Juha Alakarhu, 'Image Sensors and Image Quality in Mobile Phones' *International Image Sensor Workshop*, Jun. 2007.

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority to and the benefit of Korean Patent Application No. 10-2019-0075908, filed in the Korean Intellectual Property Office on Jun. 25, 2019, the entire contents of which are incorporated herein by reference.

BACKGROUND

1. Field

Example embodiments provide a compound and a photoelectric device, an image sensor, and an electronic device including the same.

2. Description of the Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

The organic material has a high absorption coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in the green wavelength region and maintaining good efficiency even under high temperature conditions.

Example embodiments also provide an image sensor including the photoelectric device (e.g., organic photoelectric device).

Example embodiments also provide an electronic device including the image sensor.

According to example embodiments, a compound is represented by Chemical Formula 1.

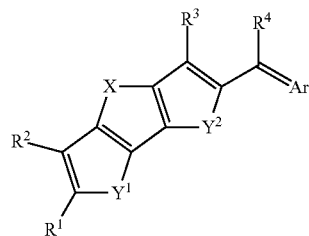

[Chemical Formula 1]

In Chemical Formula 1,

Ar is a substituted or unsubstituted C6 to C30 hydrocarbon cyclic group a substituted or unsubstituted C2 to C30 heterocyclic group or a fused ring thereof, Ar has at least one functional group selected from C=O, C=S, C=Se, and C=Te, X is O, S, Se, Te, S(=O), S(=O)$_2$, SiR$^a$R$^b$, GeR$^c$R$^d$, or CR$^e$R$^f$ (wherein R$^a$, R$^b$, R$^c$, R$^d$, R$^e$, and R$^f$ are independently hydrogen or a substituted or unsubstituted C1 to C10 alkyl group, and wherein R$^a$, R$^b$, R$^c$, R$^d$, R$^e$, and R$^f$ are independently present and R$^a$ and R$^b$, R$^c$ and R$^d$, or R$^e$ and R$^f$ are linked to each other to provide a spiro structure), Y$^1$ and Y$^2$ are independently O, S, Se, or Te, and R$^1$ to R$^4$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$, and R$^c$ are independently hydrogen or a substituted or unsubstituted C1 to C10 alkyl group), or a combination thereof, or adjacent two groups of R$^1$ to R$^4$ are linked to each other to provide a substituted or unsubstituted C5 to C30 hydrocarbon cyclic group or a substituted or unsubstituted C2 to C30 heterocyclic group. In Chemical Formula 1, Y$^1$ and Y$^2$ may be the same or different. In addition, X may be the same as or different from Y$^1$ and Y$^2$.

In some embodiments, in Chemical Formula 1, X may be one of S, Se, and Te and Y$^1$ and Y$^2$ independently may be one of S, Se, and Te. In Chemical Formula 1, X may be one of SiR$^a$R$^b$, GeR$^c$R$^d$, and CR$^e$R$^f$ and Y$^1$ and Y$^2$ independently may be one of O, S, Se, and Te.

In some embodiments, in Chemical Formula 1, Ar may be a cyclic group represented by Chemical Formula 3.

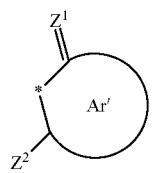

[Chemical Formula 3]

In Chemical Formula 3,

Ar' is a substituted or unsubstituted C6 to C30 aryl group or a substituted or unsubstituted C3 to C30 heteroaryl group, Z$^1$ is O, S, Se, or Te, and $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

In some embodiments, in Chemical Formula 1, Ar may be a cyclic group represented by one of Chemical Formulae 4A to 4F.

[Chemical Formula 4A]

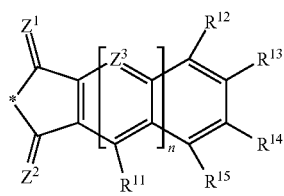

In Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen, deuterium, or a substituted or unsubstituted C1 to C10 alkyl group), $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{11}$, $R^{12}$, $R^{13}$, $R^{14}$, and $R^{15}$ are independently present or at least one of $R^{12}$ and $R^{13}$ and $R^{14}$ and $R^{15}$ is linked with each other to provide a fused aromatic ring, n is 0 or 1, and \* is a linking position.

[Chemical Formula 4B]

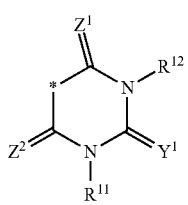

In Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and \* is a linking position.

[Chemical Formula 4C]

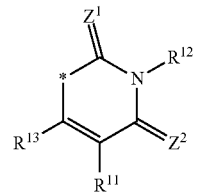

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and \* is a linking position.

[Chemical Formula 4D]

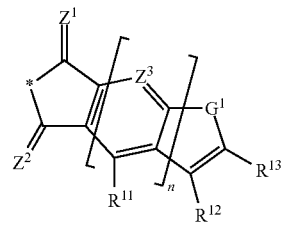

In Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and \* is a linking position.

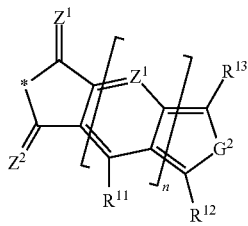

[Chemical Formula 4E]

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^4$ is N or $CR^c$ (wherein $R^c$ is hydrogen or a substituted or unsubstituted C1 to C10 alkyl group), $G^2$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking position.

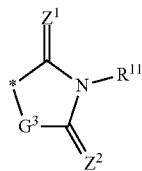

[Chemical Formula 4F]

In Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

In some embodiments, the compound represented by Chemical Formula 1 may have an aspect ratio (Z/X) of less than or equal to about 0.30. The aspect ratio may be obtained by dividing a shortest length (Z) of the compound by a longest length (X) of the compound.

In some embodiments, the compound may have a maximum absorption wavelength ($\lambda_{max}$) in a wavelength range of greater than or equal to about 500 nm and less than or equal to about 580 nm, for example greater than or equal to about 520 nm and less than or equal to about 555 nm in a thin film state.

In some embodiments, the compound may exhibit a light absorption curve having a full width at half maximum (FWHM) of about 50 nm to about 120 nm.

In some embodiments, a difference between a melting point of the compound and a temperature at which 10 wt % of an initial weight is lost (deposition temperature) may be greater than or equal to about 10° C.

According to another embodiment, a photoelectric device (e.g., organic photoelectric device) includes a first electrode and a second electrode facing each other and an active layer interposed between the first electrode and the second electrode, wherein the active layer includes the compound represented by Chemical Formula 1.

According to another embodiment, an image sensor includes the photoelectric device.

In some embodiments, the image sensor may include a semiconductor substrate integrated with a plurality of first photo-sensing devices configured to sense light in a blue wavelength region and a plurality of second photo-sensing devices configured to sense light in a red wavelength region, and the photoelectric device may be on the semiconductor substrate and configured to sense light in a green wavelength region.

In some embodiments, the image sensor may further include a color filter layer comprising a blue filter configured to selectively transmit light in a blue wavelength region and a red filter configured to selectively transmit light in a red wavelength region.

In some embodiments, the first photo-sensing device and the second photo-sensing device may be stacked in a vertical direction in the semiconductor substrate.

In some embodiments, the image sensor may include a green photoelectric device which is the photoelectric device, a blue photoelectric device configured to selectively absorb light in a blue wavelength region, and a red photoelectric device configured to selectively absorb light in a red wavelength region. The blue photoelectric device and the red photoelectric device may be stacked.

According to another embodiment, an electronic device includes the image sensor.

The compound may selectively absorb light in a green wavelength region and may have thermal stability and charge mobility. The compound improves efficiency of the device by increasing wavelength selectivity of the green wavelength region and provides photoelectric devices, image sensors and electronic devices that do not deteriorate performance even at high temperature processes due to improved thermal stability.

DETAILED DESCRIPTION

Figure 1:
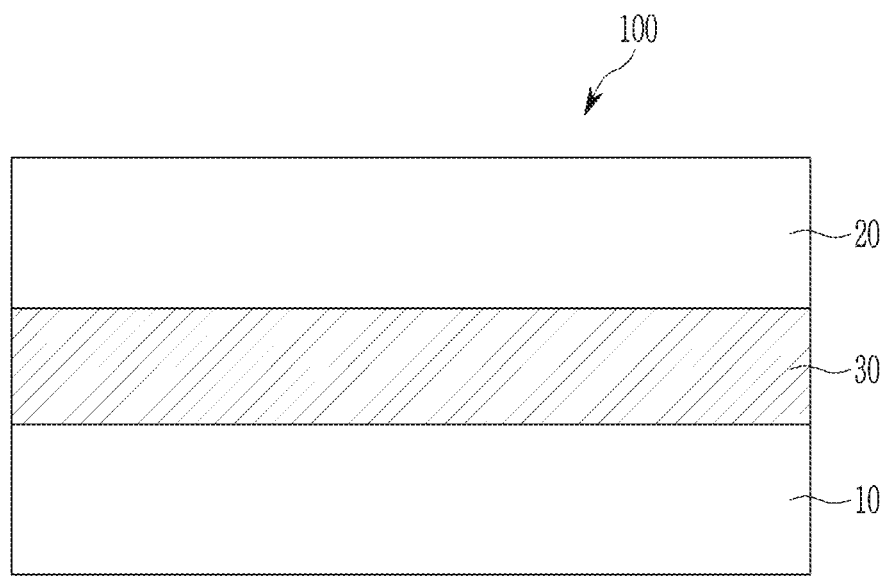
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; A and B; A and C; B and C; or A, B, and C).

As used herein, when a specific definition is not otherwise provided, "substituted" refers to replacement of a hydrogen of a compound or a functional group by a substituent selected from a halogen atom (F, Br, Cl, or I), a hydroxy group, a nitro group, a cyano group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when a specific definition is not otherwise provided, "'hetero" refers to one including 1 to 3 heteroatoms selected from N, O, S, Se, Te, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a substituent including all element of the functional group having p-orbitals which form conjugation, and may be a monocyclic, polycyclic or fused ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, "hydrocarbon cyclic group" may be a C3 to C30 hydrocarbon cyclic group. The hydrocarbon cyclic group may be an arene group (e.g., C6 to C30 aryl group, C6 to C20 aryl group, or C6 to C10 aryl group), an alicyclic hydrocarbon cyclic group (e.g., C3 to C30 cycloalkyl group, C5 to C30 cycloalkyl group, C3 to C20 cycloalkyl group, or C3 to C10 cycloalkyl group), or a fused ring group. For example, the fused ring group refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a C2 to C30 heterocyclic group. The heterocyclic group refers to a cyclic group including a heteroatom selected from N, O, S, Se, Te, P, and Si instead of at least one, for example, 1 to 3 carbon atoms in a cyclic group selected from an arene group (e.g., C6 to C30 aryl group, C6 to C20 aryl group or C6 to C10 aryl group), an alicyclic hydrocarbon group (e.g., C3 to C30 cycloalkyl group, C3 to C20 cycloalkyl group, or C3 to C10 cycloalkyl group), and a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P, and Si in a cyclic group.

As used herein, "C6 to C30 aromatic hydrocarbon group" includes a C6 to C30 aryl group such as a phenyl group or a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited to.

As used herein, "aromatic ring" refers to a C5 to C12 cyclic group (e.g., C6 to C12 aryl group) that provides a conjugated structure or a C2 to C10 heterocyclic group (e.g., C2 to C4 heteroaryl group) that provides a conjugated structure).

Hereinafter, a compound according to an embodiment is described. The compound is represented by Chemical Formula 1.

[Chemical Formula 1]

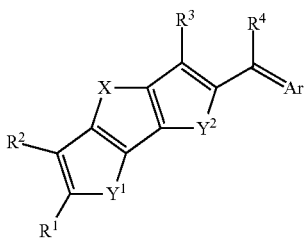

In Chemical Formula 1,

Ar is a substituted or unsubstituted C2 to C30 hydrocarbon cyclic group having at least one functional group selected from C=O, C=S, C=Se, and C=Te, a substituted or unsubstituted C6 to C30 heterocyclic group having at least one functional group selected from C=O, C=S, C=Se, and C=Te, or a fused ring thereof, X is O, S, Se, Te, S(=O), S(=O)$_2$, SiR$^a$R$^b$, GeR$^c$R$^d$, or CR$^e$R$^f$ (wherein R$^a$, R$^b$, R$^c$, R$^d$, R$^e$, and R$^f$ are independently hydrogen or a substituted or unsubstituted C1 to C10 alkyl group, and wherein R$^a$, R$^b$, R$^c$, R$^d$, R$^e$, and R$^f$ are independently present and R$^a$ and R$^b$, R$^c$ and R$^d$, or R$^e$ and R$^f$ are linked to each other to provide a spiro structure), Y$^1$ and Y$^2$ are independently O, S, Se, or Te, and R$^1$ to R$^4$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$, and R$^c$ are independently hydrogen or a substituted or unsubstituted C1 to C10 alkyl group), or a combination thereof, or adjacent two groups of R$^1$ to R$^4$ are linked to each other to provide a substituted or unsubstituted C5 to C30 hydrocarbon cyclic group or a substituted or unsubstituted C2 to C30 heterocyclic group.

The compound represented by Chemical Formula 1 includes an electron donor moiety of an aromatic ring including heteroatoms (X, Y$^1$, and Y$^2$) and an electron acceptor moiety represented by Ar. In Chemical Formula 1, the electron donor moiety may induce a planar structure and thus improve charge mobility.

The compound represented by Chemical Formula 1 may have an aspect ratio (Z/X) obtained by dividing the shortest length (Z) by the longest length (X) in a range of less than or equal to about 0.30, for example less than or equal to about 0.25 or less than or equal to about 0.20. Within the range, the compound may maintain excellent planarity, and accordingly, the charge mobility thereof may be improved.

In Chemical Formula 1, R$^1$ to R$^3$ include no amine group. Accordingly, the structure of Chemical Formula 1 has a donor-acceptor structure. Accordingly, an absorption wavelength may be adjusted within a green wavelength range (about 500 nm to about 580 nm), a deposition temperature may be decreased, and an absorption coefficient may be increased.

Since R$^1$ and R$^2$ substituted in the aromatic ring containing heteroatoms (X, Y$^1$, and Y$^2$) in Chemical Formula 1 do not include an amine group, all atoms constituting the compound are positioned in a plane so that the aspect ratio of the compound is controlled to be small to improve planarity.

When X is SiR$^a$R$^b$, GeR$^c$R$^d$, or CR$^e$R$^f$ in Chemical Formula 1, R$^a$ and R$^b$, R$^c$ and R$^d$, or R$^e$ and R$^f$ may be independently of each other or may be linked to each other to form a spiro structure. The spiro structure may be a substituted or unsubstituted C5 to C30 hydrocarbon cyclic group or a substituted or unsubstituted C2 to C30 heterocyclic group. The C5 to C30 hydrocarbon cyclic group may be, for example, a C5 to C30 cycloalkyl group (e.g., C3 to C20 cycloalkyl group or C3 to C10 cycloalkyl group) and the substituted or unsubstituted C2 to C30 heterocyclic group may be, for example, a C2 to C20 heterocycloalkyl group or a C2 to C10 heterocycloalkyl group.

When R$^a$ and R$^b$, R$^c$ and R$^d$, or R$^e$ and R$^f$ are linked with each other to provide a spiro structure, the compound represented by Chemical Formula 1 may be represented by Chemical Formula 2A or Chemical Formula 2B.

[Chemical Formula 2A]

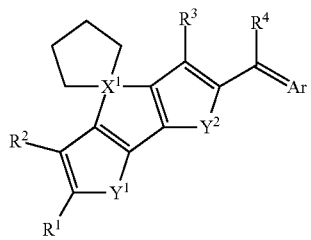

[Chemical Formula 2B]

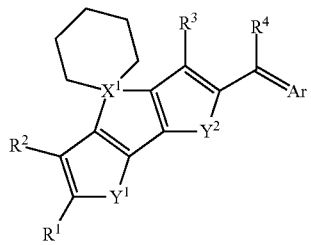

In Chemical Formulae 2A and 2B,

Ar, Y$^1$, Y$^2$, and R$^1$ to R$^4$ are the same as Chemical Formula 1 and X$^1$ is Si, Ge, or C.

In Chemical Formula 1, Ar may be represented by Chemical Formula 3.

[Chemical Formula 3]

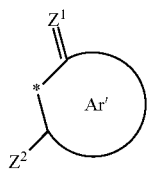

In Chemical Formula 3,

Ar' is a substituted or unsubstituted C6 to C30 aryl group or a substituted or unsubstituted C3 to C30 heteroaryl group, $Z^1$ is O, S, Se, or Te, and $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

In Chemical Formula 1, Ar may be a cyclic group represented by one of Chemical Formulae 4A to 4F.

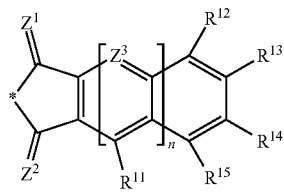

[Chemical Formula 4A]

In Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen, deuterium, or a substituted or unsubstituted C1 to C10 alkyl group), $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{11}$, $R^{12}$, $R^{13}$, $R^{14}$, and $R^{15}$ are independently present or at least one of $R^{12}$ and $R^{13}$ and $R^{14}$ and $R^{15}$ is linked with each other to provide a fused aromatic ring, n is 0 or 1, and

* is a linking position.

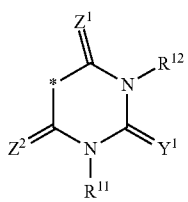

[Chemical Formula 4B]

In Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking position.

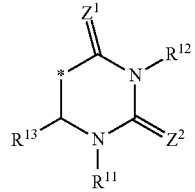

[Chemical Formula 4C]

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position.

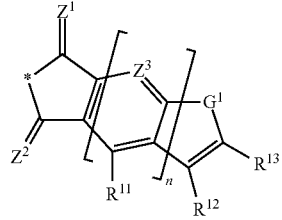

[Chemical Formula 4D]

In Chemical Formula 4D, $Z^1$ is O, S, Se, or Te, and $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and

* is a linking position.

[Chemical Formula 4E]

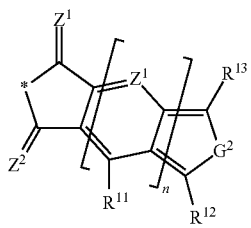

In Chemical Formula 4E,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^4$ is N or $CR^c$ (wherein $R^c$ is hydrogen or a substituted or unsubstituted C1 to C10 alkyl group),
$G^2$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof,
n is 0 or 1, and
* is a linking position.

[Chemical Formula 4F]

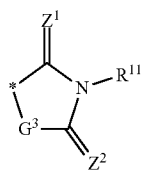

In Chemical Formula 4F,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and
$G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

The cyclic group represented by Chemical Formula 4A may be a cyclic group represented by Chemical Formula 4A-1 or Chemical Formula 4A-2.

[Chemical Formula 4A-1]

[Chemical Formula 4A-2]

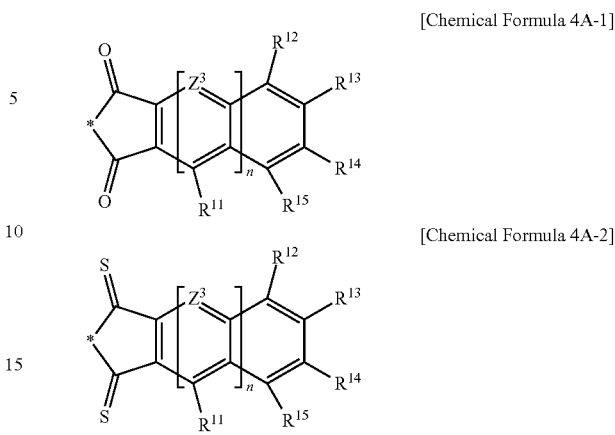

In Chemical Formulae 4A-1 and 4A-2,
$Z^3$, $R^{11}$, n, $R^{11}$, $R^{12}$, $R^{13}$, $R^{14}$, and $R^{15}$ are the same as in Chemical Formula 4A.

When $R^{12}$ and $R^{13}$ and/or $R^{14}$ and $R^{15}$ of the cyclic group represented by Chemical Formula 4A are independently linked with each other to provide a fused aromatic ring, it may be a cyclic group represented by Chemical Formula 4A-3.

[Chemical Formula 4A-3]

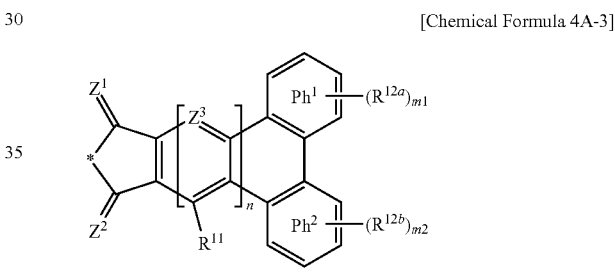

In Chemical Formula 4A-3,
$Z^1$, $Z^2$, $Z^3$, $R^{11}$, and n are the same as in Chemical Formula 4A,
$R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof,
m1 and m2 are independently integers of 0 to 4, and
Ph1 and Ph2 are fused phenylene rings and one of Ph1 and Ph2 may optionally be omitted.

The cyclic group represented by Chemical Formula 4B may be, for example, a cyclic group represented by Chemical Formula 4B-1, 4B-2, or 4B-3.

[Chemical Formula 4B-1]

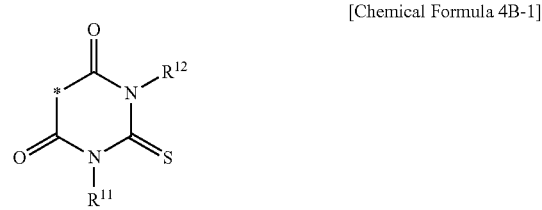

-continued

[Chemical Formula 4B-2]

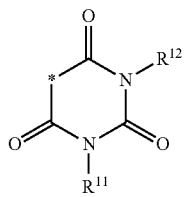

[Chemical Formula 4B-3]

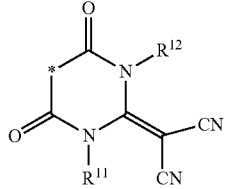

In Chemical Formulae 4B-1, 4B-2, and 4B-3,
$R^{11}$ and $R^{12}$ are the same as in Chemical Formula 4B.

The cyclic group represented by Chemical Formula 4C may be, for example, a cyclic group represented by Chemical Formula 4C-1 or 4C-3.

[Chemical Formula 4C-1]

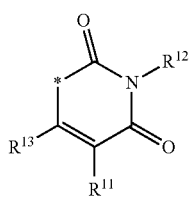

[Chemical Formula 4C-2]

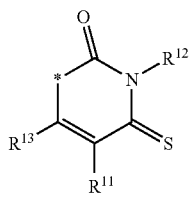

In Chemical Formulae 4C-1 and 4C-2,
$R^{11}$ to $R^{13}$ are the same as in Chemical Formula 4C.

In Chemical Formula 1, the heteroatoms (X, $Y^1$, and $Y^2$) of the electron donor moiety and $Z^1$ and $Z^2$ (O, S, Se, and Te) of the electron acceptor moiety increase intramolecular interactions and thus the absorption intensity at a specific wavelength may be improved.

Specific examples of the compound of Chemical Formula 1 may be a compound of Chemical Formula 5A, Chemical Formula 5B, Chemical Formula 5C, Chemical Formula 5D, Chemical Formula 5E, or Chemical Formula 5F, but is not limited thereto.

[Chemical Formula 5A]

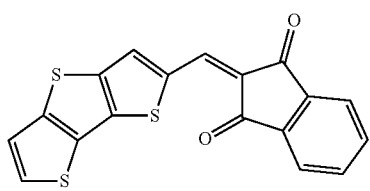

-continued

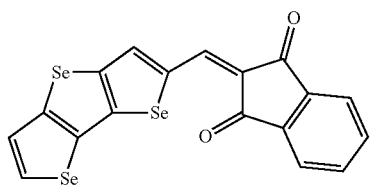

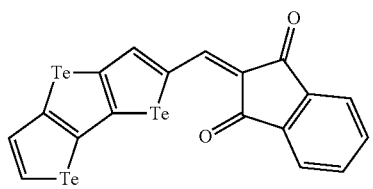

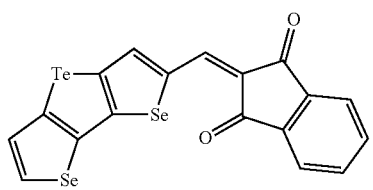

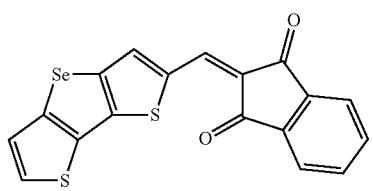

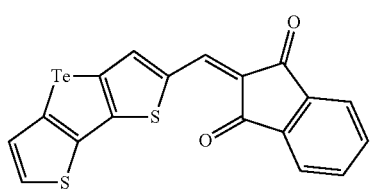

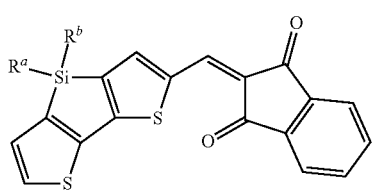

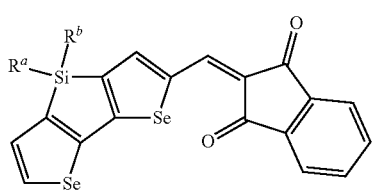

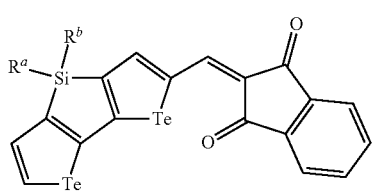

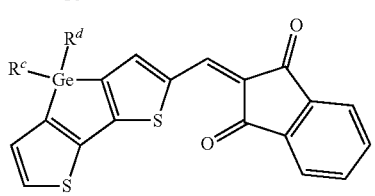

17

-continued

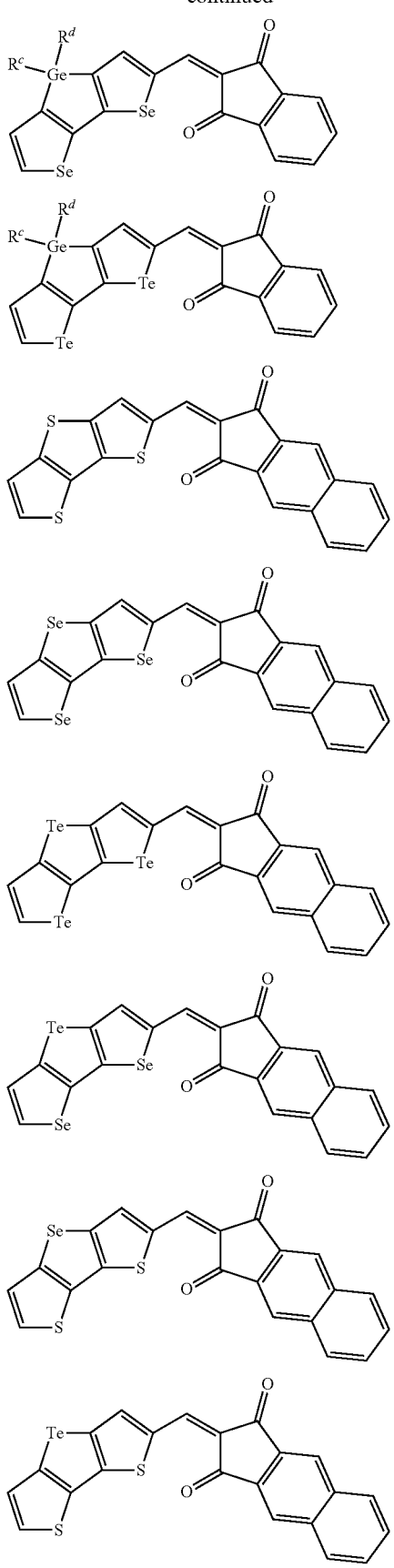

18

-continued

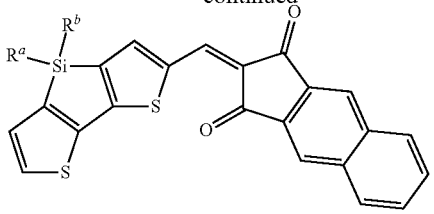
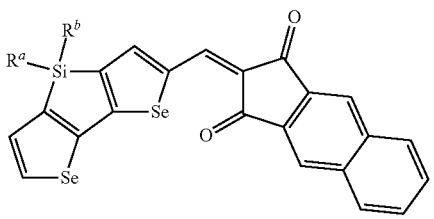
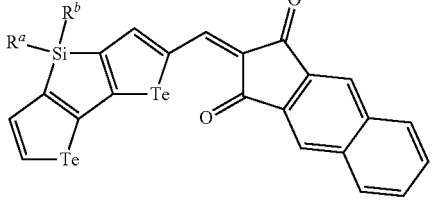
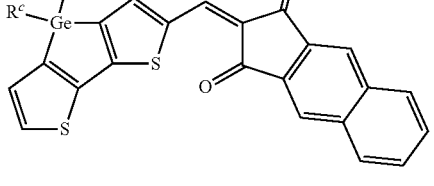
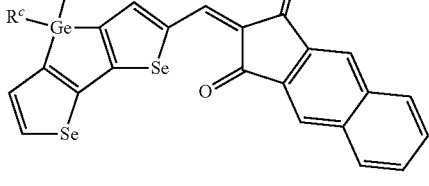
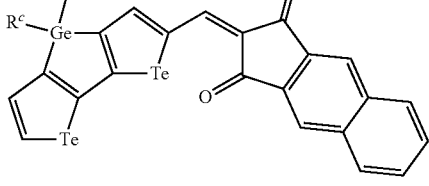
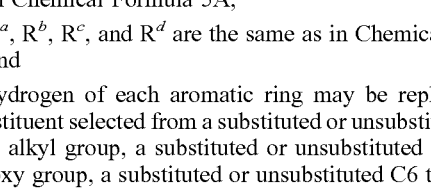

In Chemical Formula 5A, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

[Chemical Formula 5B]

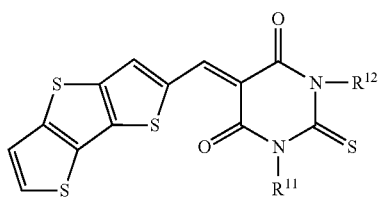
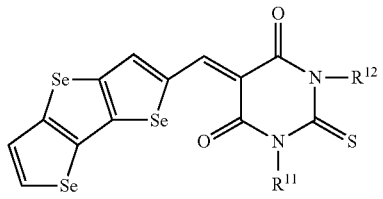
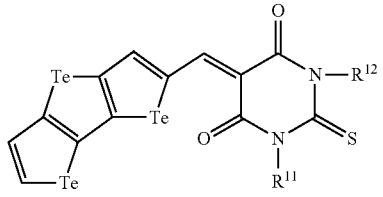
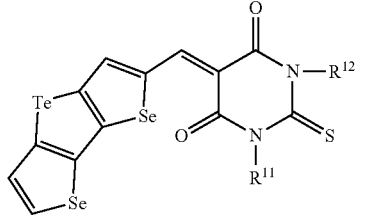
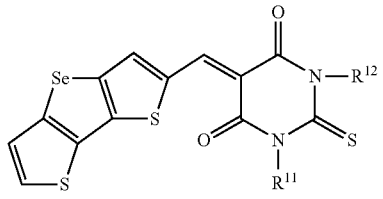
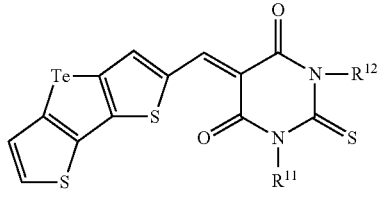
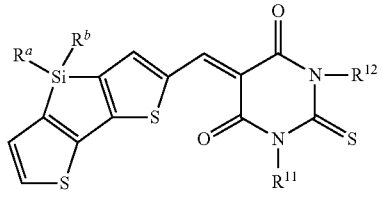
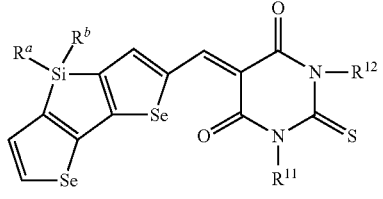
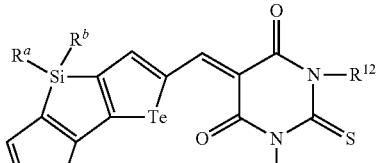
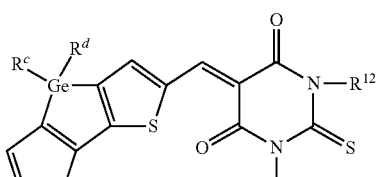
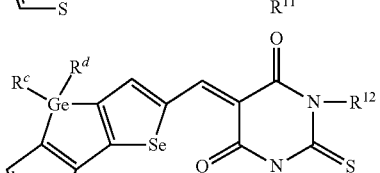
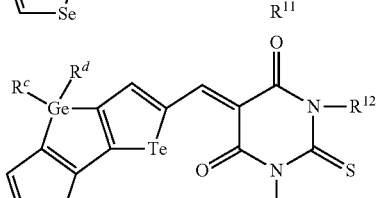
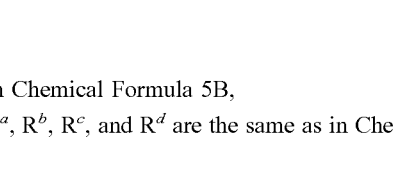

In Chemical Formula 5B, $R^a$, $R^b$, $R^c$, and $R^d$ are the same as in Chemical Formula 1, $R^{11}$ and $R^{12}$ are the same as in Chemical Formula 4B, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

[Chemical Formula 5C]

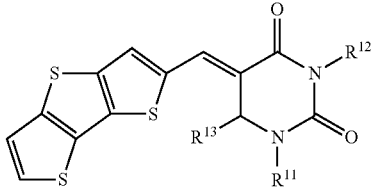
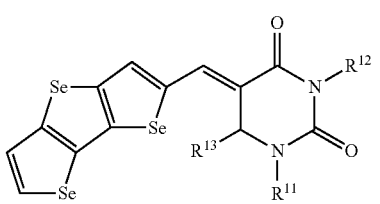

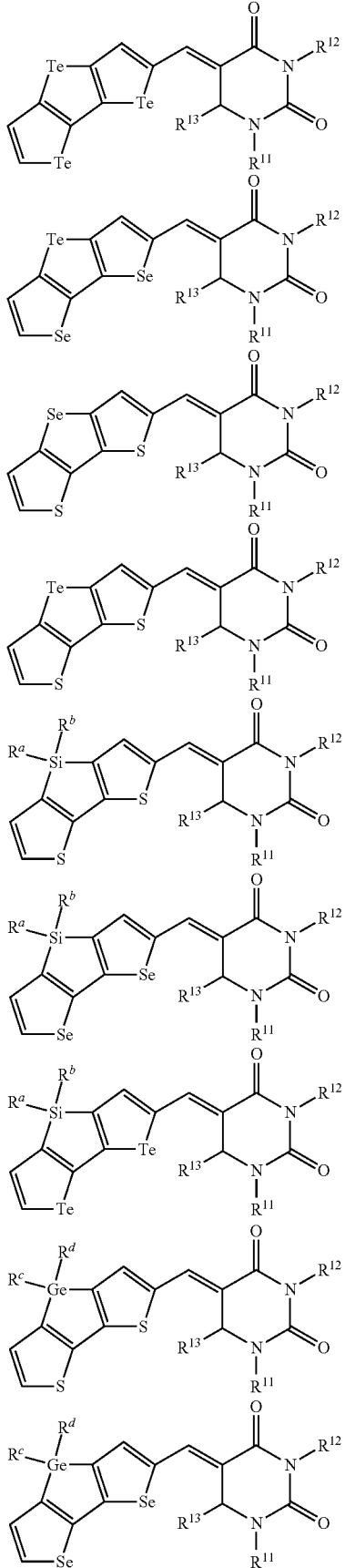

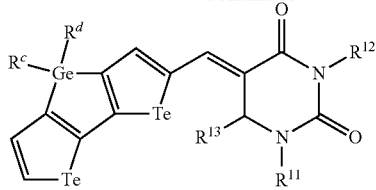

In Chemical Formula 5C, $R^a$, $R^b$, $R^c$, and $R^d$ are the same as in Chemical Formula 1, $R^{11}$ to $R^{13}$ are the same as in Chemical Formula 4C, and, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

[Chemical Formula 5D]

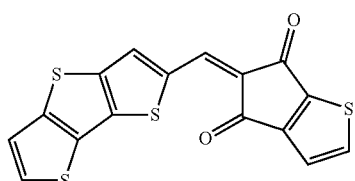

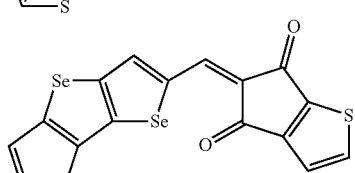

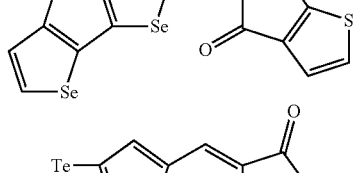

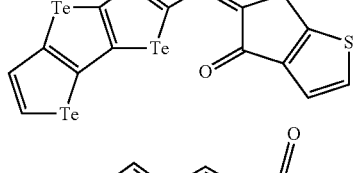

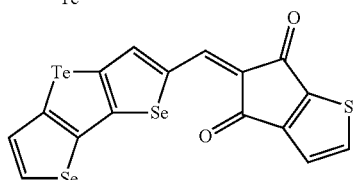

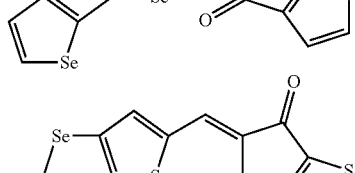

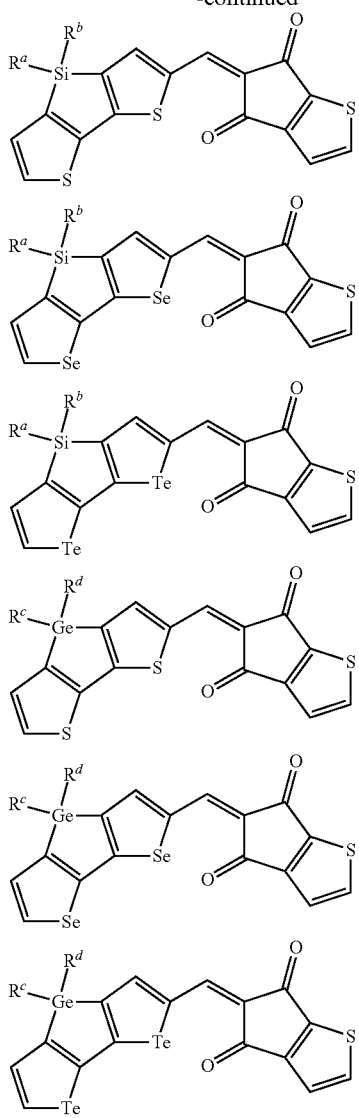

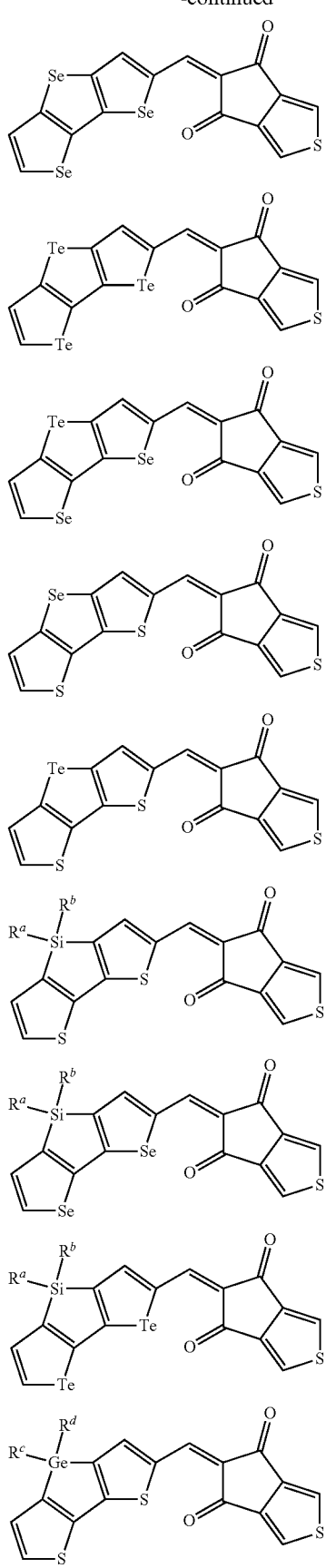

In Chemical Formula 5D, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

[Chemical Formula 5E]

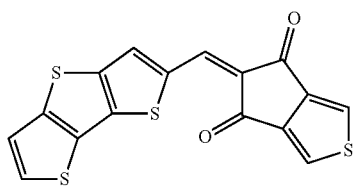

-continued

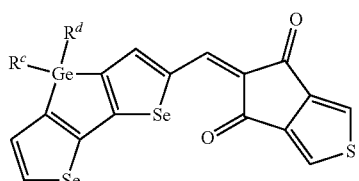

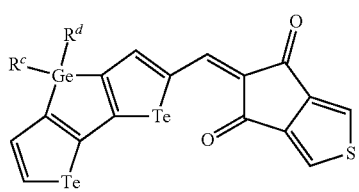

In Chemical Formula 5E, $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

[Chemical Formula 5F]

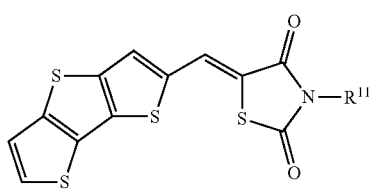

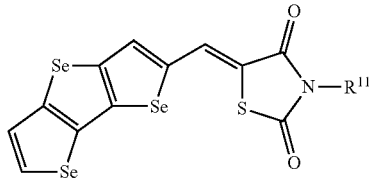

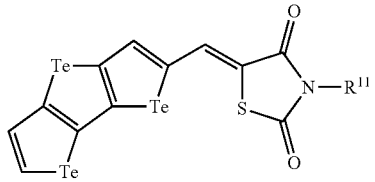

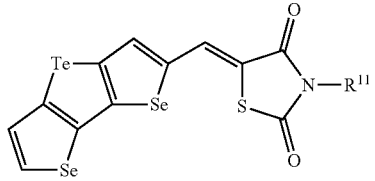

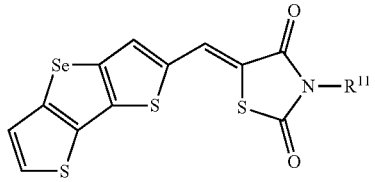

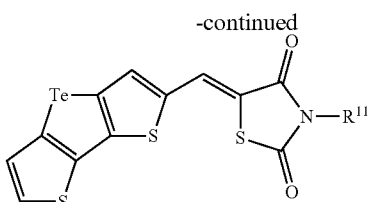

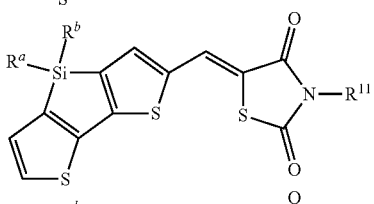

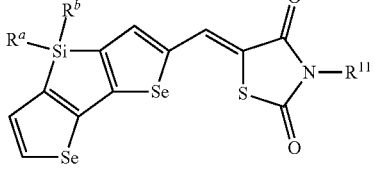

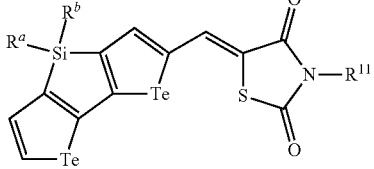

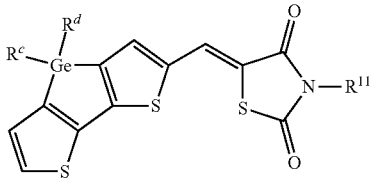

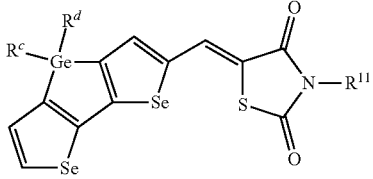

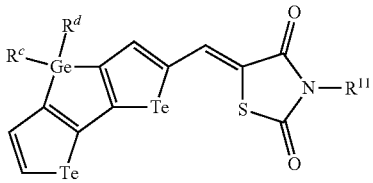

In Chemical Formula 5F, $R^{11}$ is the same as in Chemical Formula 4F $R^a$, $R^b$, $R^c$, and $R^d$ are the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof.

The compound may selectively absorb light in a green wavelength region, and may have a maximum absorption wavelength ($\lambda_{max}$) in a wavelength region of about 500 nm to about 580 nm, for example about 520 nm to about 555 nm.

The compound may exhibit alight absorption curve having a full width at half maximum (FWHM) of about 50 nm to about 120 nm, for example about 50 nm to about 110 nm or about 50 nm to about 100 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated.

Accordingly, the compound desirably has a higher melting point than the deposition temperature. In this regard, the compound has a melting point higher than the deposition temperature, for example, about 10° C. or higher, about 15° C. or higher, about 20° C. or higher, about 25° C. or higher, or about 30° C. or higher, and thus may be desirably used in the deposition process.

In more detail, the donor-acceptor-type material represented by the structure of Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Since such a material cannot produce a stable image sensor, $T_m$ should be higher than $T_s$, and $T_m - T_s \geq 10°$ C. is more desirable.

In addition, a micro lens array (MLA) needs to be formed to concentrate light after manufacturing an organic photoelectric device during manufacture of an image sensor. This micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be prevented from the deterioration by the heat treatment. The compound may be suppressed from the thermal vibration of molecules due to a conjugation structure in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO energy level than an n-type semiconductor. For example, when the compound is mixed with an n-type material such as fullerene, the compound desirably has a higher LUMO energy level than 4.2 eV than the fullerene having a LUMO energy level of 4.2 eV. As for the appropriate HOMO-LUMO energy level of the compound, when the compound has a HOMO energy level ranging from about 5.2 eV to about 5.8 eV and an energy bandgap ranging from about 2.12 eV to about 2.48 eV, the LUMO energy level of the compound is in a range of about 3.8 eV to about 2.7 eV. The compound having a HOMO energy level, an LUMO energy level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound may selectively absorb light in a green wavelength region, and the active layer 30 including the compound may have a maximum absorption wavelength ($\lambda_{max}$) in a wavelength region of about 500 nm to about 580 nm, for example about 520 nm to about 570 nm or about 520 nm to about 555 nm.

The active layer 30 may exhibit a light absorption curve having a relatively narrow full width at half maximum (FWHM) of about 50 nm to about 120 nm, about 50 nm to about 110 nm, or about 50 nm to about 100 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$.

The active layer 30 may further include an n-type semiconductor compound for forming pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 6.

[Chemical Formula 6]

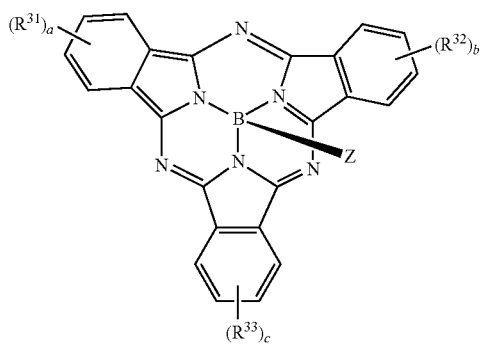

In Chemical Formula 6, $R^{31}$ to $R^{33}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers of 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 7 or 8, but is not limited thereto.

[Chemical Formula 7]

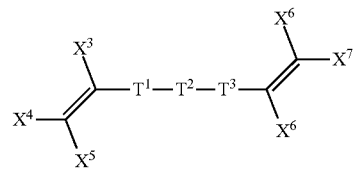

[Chemical Formula 8]

$EWG^1—T^1—T^2—T^3—EWG^2$

In Chemical Formulae 8 and 9, $T^1$, $T^2$, and $T^3$ are aromatic rings including substituted or unsubstituted thiophene moieties, $T^1$, $T^2$, and $T^3$ are independently present or are fused to each other, $X^3$ to $X^8$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are independently electron withdrawing groups.

For example, in Chemical Formula 7, at least one of $X^3$ to $X^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

[Chemical Formula 9]

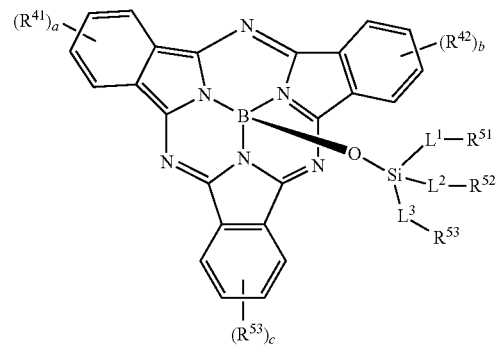

In Chemical Formula 9, $R^{41}$ to $R^{43}$ are independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are independently a single bond, a substituted or unsubstituted C1 to C30 alkylene group, a substituted or unsubstituted C6 to C30 arylene group, divalent a substituted or unsubstituted C3 to C30 heterocyclic group, or a combination thereof, $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently integer of 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90% or more.

In the photoelectric device 100, when light enters from the first electrode 10 and/or second electrode 20, and when the active layer 30 absorbs light in a predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
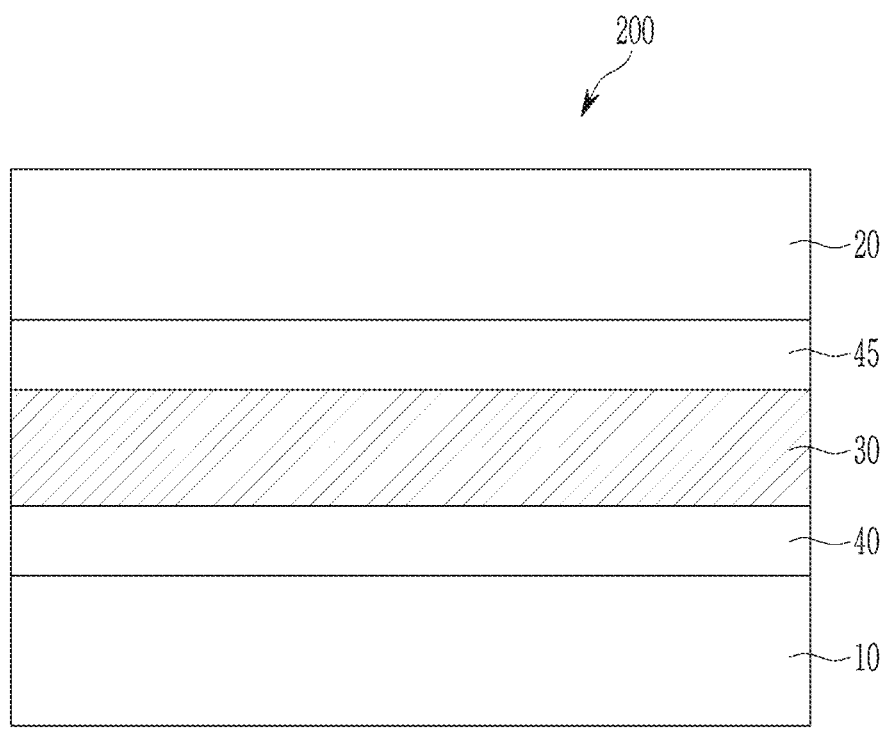
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. For example, the charge auxiliary layer 45 may be between the active layer 30 and the second electrode 20 and/or the charge auxiliary layer 40 may be between the active layer 30 and the first electrode 10. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
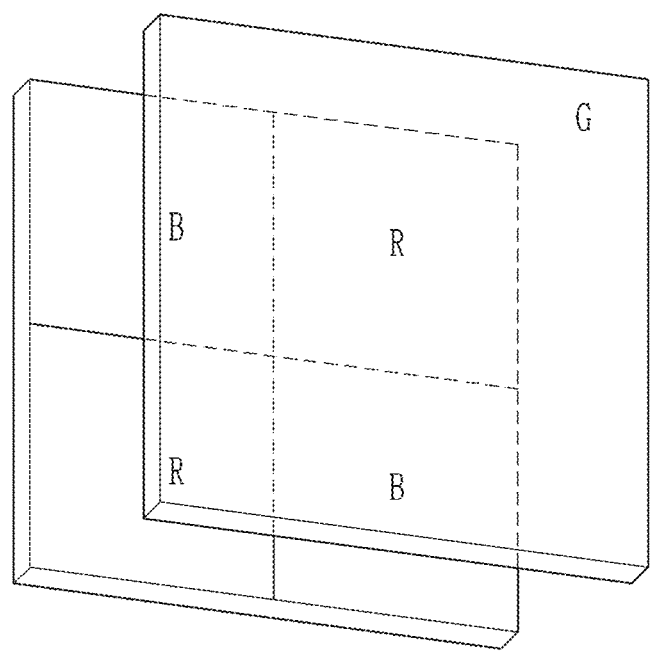
FIG. 3 is a schematic top plan view showing an organic CMOS image sensor according to an embodiment.
Figure 4:
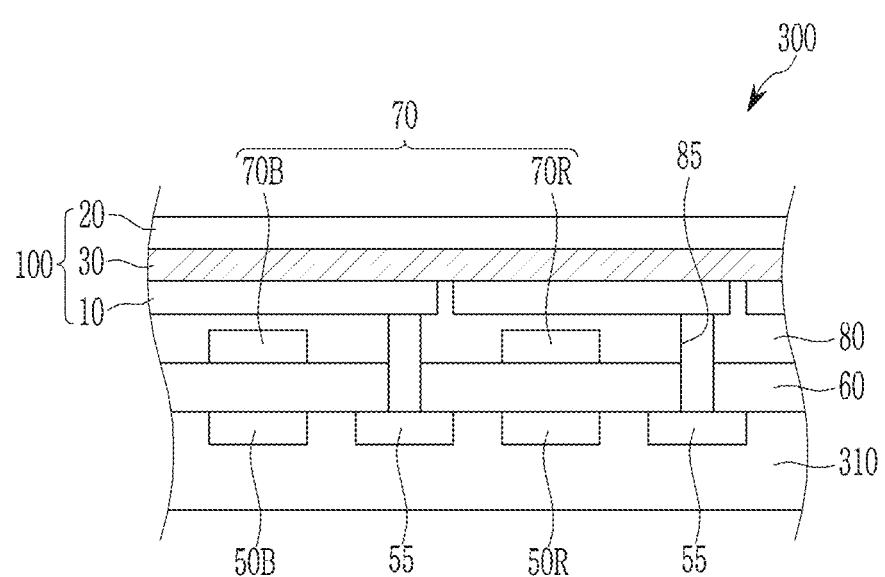
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
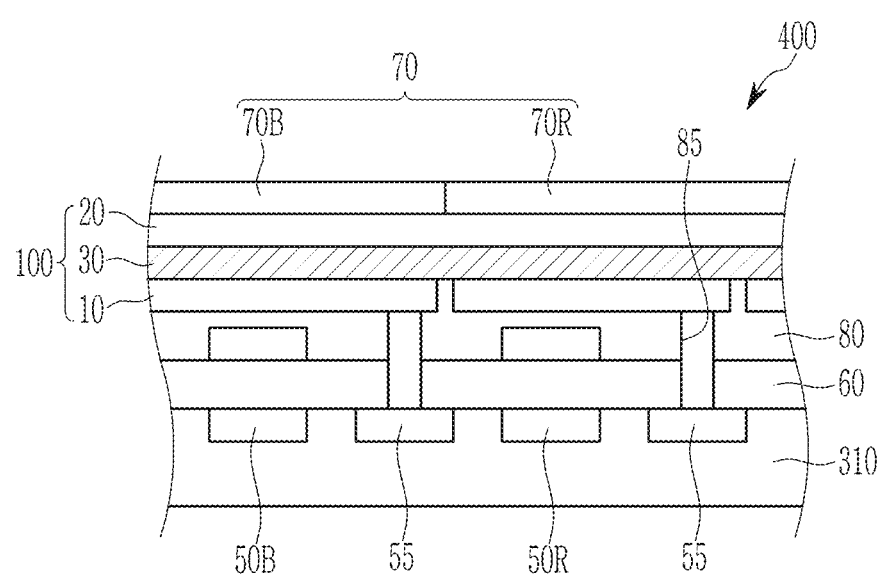
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
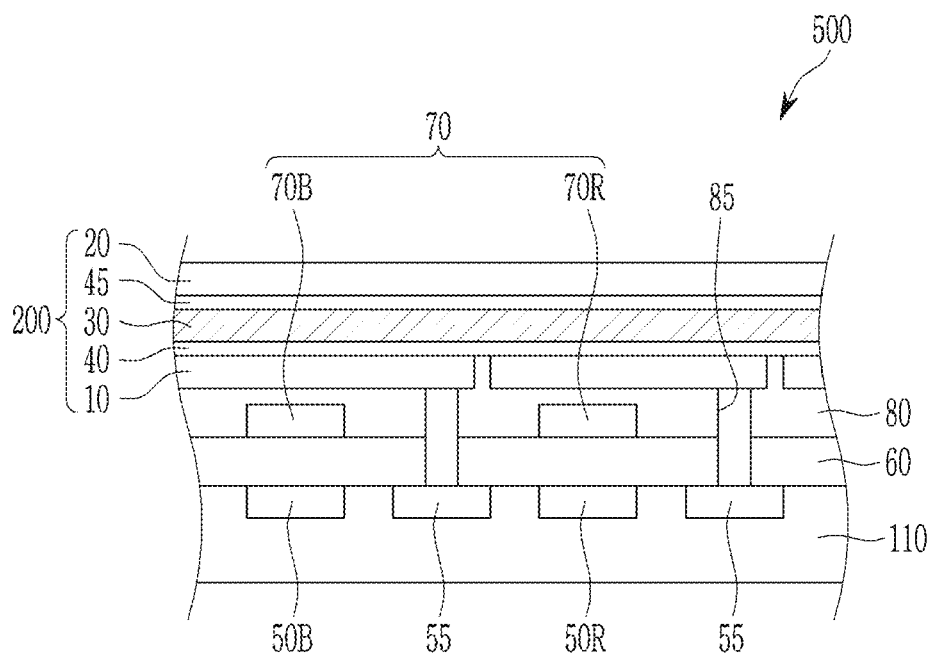
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
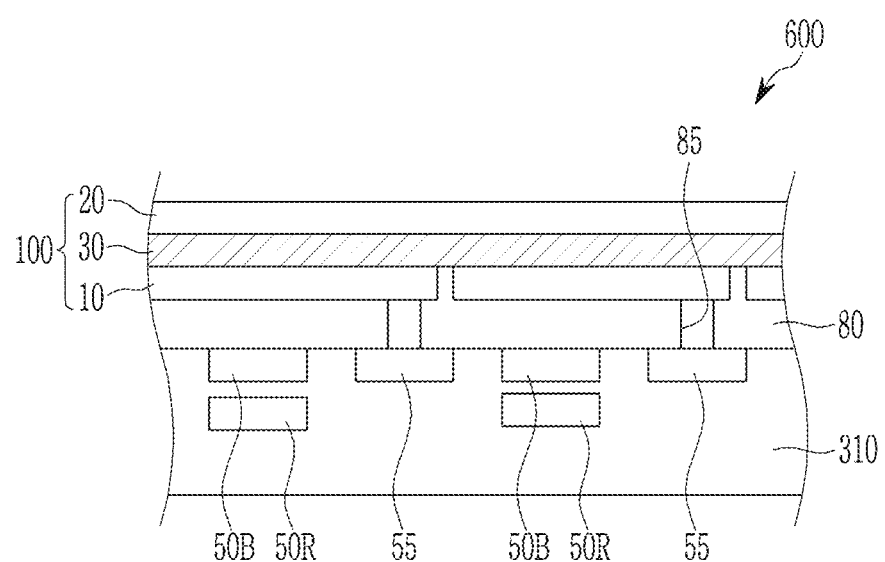
FIG. 7 is a schematic view showing an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
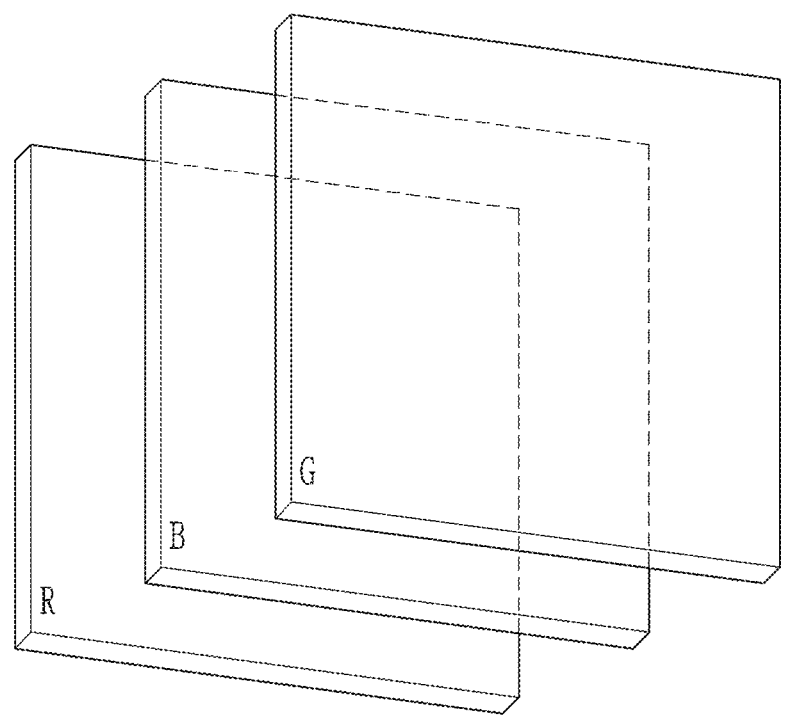
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the aforementioned photoelectric device 100 or photoelectric device 200, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the green photoelectric device (G) selectively absorbing light in a green wavelength region, the blue photoelectric device (B) selectively absorbing light in a red wavelength region, and the red photoelectric device (R) selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility ($\Delta E^*ab$) despite a stacked structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility ($\Delta E^*ab$) shows a difference from standard colors in an X-Rite chart, and the $\Delta E^*ab$ is defined as a distance between two points on a L*a*b* color space by CIE (Commission International de L' Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1, $\Delta L^*$ denotes a change of a color coordinate L* compared with the color coordinate L* at room temperature (about 20° C. to about 25° C.), $\Delta a^*$ denotes a change of a color coordinate a* compared with the color coordinate a* at room temperature, and $\Delta b^*$ denotes a change of a color coordinate b* compared with the color coordinate b* at room temperature.

In order to manufacture an image sensor having high sensitivity and high color reproducibility, YSNR10≤100 lux at $\Delta E^*ab \leq 3$, and herein, the compound may realize YSNR10≤100 lux of sensitivity and color reproducibility at $\Delta E^*ab \leq 3$.

The image sensor may be applied to various electronic devices, for example, a mobile phone, a digital camera, and the like but is not limited thereto.

Figure 9:
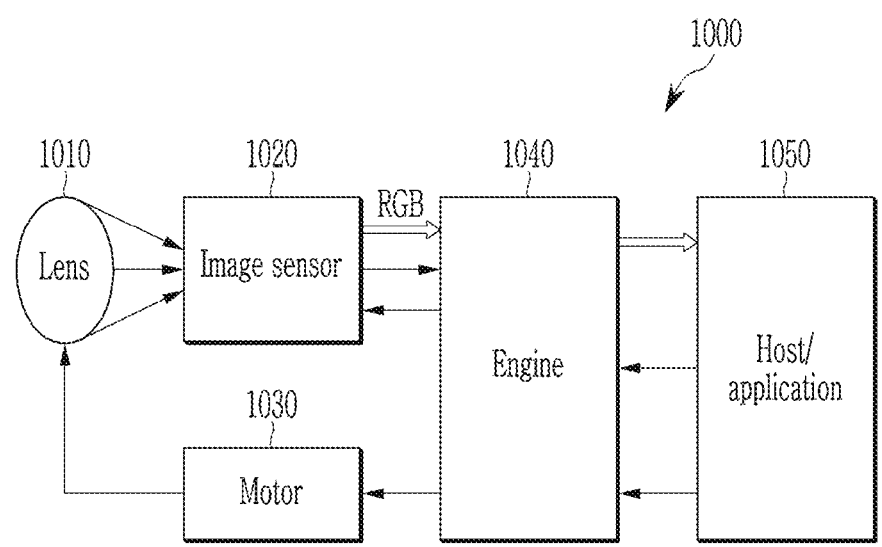
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Hereinafter, the embodiments are illustrated in more detail with reference to examples. However, these examples are exemplary, and the present disclosure is not limited thereto.

Synthesis Example 1: Synthesis of Compound Represented by Chemical Formula 1-1

[Chemical Formula 1-1]

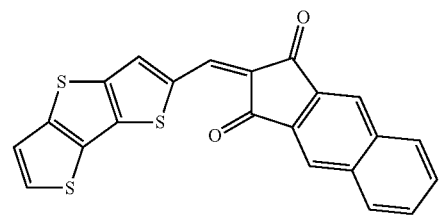

[Reaction Scheme 1-1]

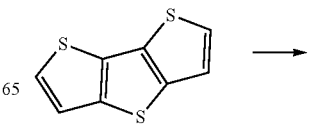

-continued 1-1A 1-1

(1) Synthesis of Compound 1-1A 2.00 g (10.19 mmol) of dithieno[3,2-b:2',3'-d]thiophene is dissolved in 30 ml of tetrahydrofuran (THF) and then, cooled down to −78° C. and stirred for 10 minutes, and 4.89 ml (12.23 mmol) of normal butyllithium is drop by drop added thereto.

After stirred at the same temperature for one hour, 1.57 ml (20.38 mmol) of dimethyl formamide (DMF) is added thereto and then, allowed to stand and stirred until cooled down to room temperature (24° C.), 10 ml of $H_2O$ is added thereto, and an organic layer therein is gathered and then, separated and purified through column chromatography to obtain 1.76 g (7.86 mmol) of Compound 1-1A (dithieno[3,2-b:2',3'-d]thiophene-2-carbaldehyde).

$^1$H NMR (300 mHz, $CD_2Cl_3$) 9.84 (s, 1H), 8.12 (s, 1H), 7.31 (d, 1H), 7.12 (d, 1H)

(2) Synthesis of Compound Represented by Chemical Formula 1-1

1.76 g (7.86 mmol) of Compound 1-1A and 1.38 g (7.07 mmol) of 1H-cyclopenta[b]naphthalene-1,3(2H)-dione are dissolved in 50 ml of a mixed solution of chloroform and ethanol in a volume ratio of 1:2, refluxed and stirred for 12 hours, and recrystallized by using chloroform methanol to obtain 1.97 g (4.74 mmol) of a compound represented by Chemical Formula 1-1.

$^1$H NMR (300 mHz, $CD_2Cl_3$) 8.86 (s, 2H), 8.47 (s, 1H), 8.17 (s, 1H), 8.15 (d, 2H), 7.79 (dd, 2H), 7.32 (d, 1H), 7.12 (d, 1H),

Synthesis Example 2: Synthesis of Compound Represented by Chemical Formula 1-2

[Reaction Scheme 1-2]

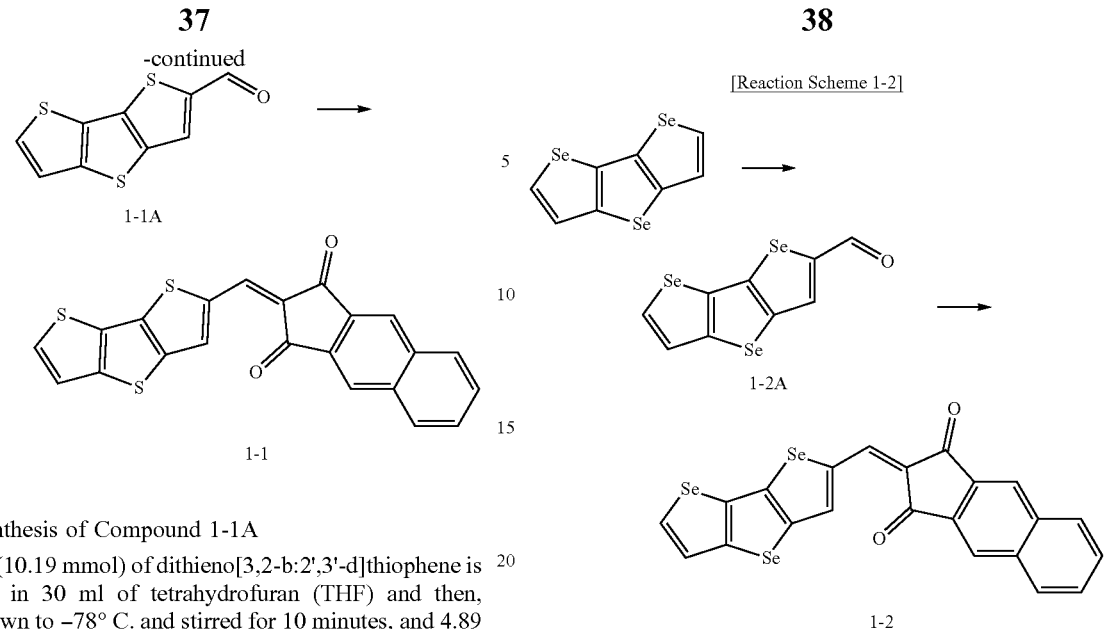

1-2A 1-2

(1) Synthesis of Compound 1-1A 2.50 g (7.41 mmol) of diseleno[3,2-b:2',3'-d]selenophene) is dissolved in 30 ml of tetrahydrofuran (THF) and then, cooled down to −78° C. and stirred for 10 minutes, and 5.56 ml (8.90 mmol) of normal butyllithium is drop by drop added thereto. After stirred at the same temperature for one hour, 1.14 ml (14.82 mmol) of dimethyl formamide (DMF) is added thereto and then, allowed to stand until cooled down to room temperature (24° C.) and stirred, 10 ml of $H_2O$ is added thereto, and an organic layer therein is separated and purified through column chromatography to obtain 1.71 g (4.67 mmol) of Compound 1-2A (diseleno[3,2-b:2',3'-d]selenophene-2-carbaldehyde).

$^1$H NMR (300 mHz, $CD_2Cl_3$) 9.71 (s, 1H), 8.11 (s, 1H), 7.68 (d, 1H), 7.10 (d, 1H)

(2) Synthesis of Compound Represented by Chemical Formula 1-2

1.71 g (4.67 mmol) of Compound 1-2A and 0.91 g (4.67 mmol) of 1H-cyclopenta[b]naphthalene-1,3(2H)-dione are dissolved in 50 ml of a mixed solution of chloroform and ethanol in a volume ratio of 1:2, refluxed and stirred for 12 hours, and recrystallized by using chloroform methanol to obtain 1.80 g (3.32 mmol) of a compound represented by Chemical Formula 1-2.

$^1$H NMR (300 mHz, $CD_2Cl_3$) 8.75 (s, 2H), 8.46 (s, 1H), 8.15 (s, 1H), 8.13 (d, 2H), 7.71 (dd, 2H), 7.27 (d, 1H), 7.09 (d, 1H),

Synthesis Example 3: Synthesis of Compound Represented by Chemical Formula 1-3

[Chemical Formula 1-2]

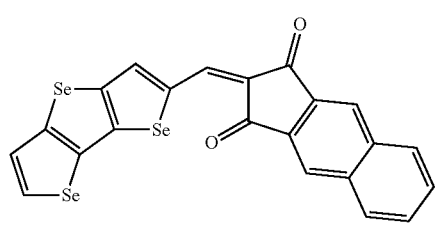

[Chemical Formula 1-3]

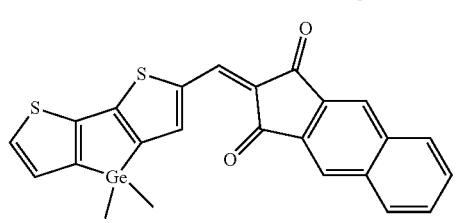

[Reaction Scheme 1-3]

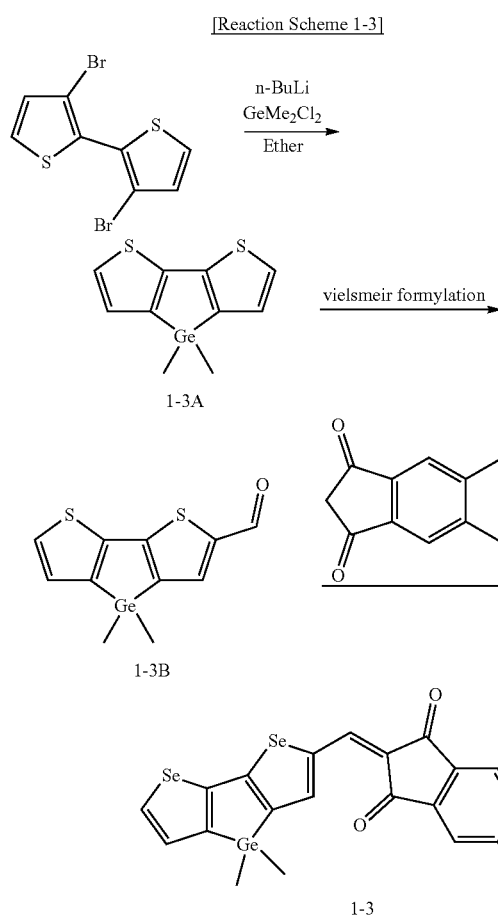

(1) Synthesis of Compound 1-3A 5.00 g (15.43 mmol) of 3,3'-dibromo-2,2'bithiophene is dissolved in 30 ml of THF, cooled down to −78° C., and stirred for 10 minutes, and 21.21 ml (33.95 mmol) of 1.6 M normal butyllithium is drop by drop added thereto. After stirred at the same temperature for one hour, 2.67 g (15.43 mmol) of dimethyldichloro germanium (GeMe$_2$Cl$_2$) is added thereto and then, allowed to stand and stirred until cooled down to room temperature and then, stirred at the room temperature for 12 hours. H$_2$O is used to extract and separate an organic layer, and the organic layer is separated and purified through column chromatography to obtain 2.26 g (8.48 mmol) of Compound 1-3A.

$^1$H NMR (300 mHz, CD$_2$Cl$_3$) 7.54 (d, 2H), 7.14 (d, 2H), 0.90 (s, 6H)

(2) Synthesis of Compound 1-3B 2.00 g (7.49 mmol) of Compound 1-3A is dissolved in 20 ml of THF and then, cooled down to −78° C. and stirred for 10 minutes, and 5.15 ml (8.24 mmol) of 1.6 M normal butyllithium is drop by drop added thereto. After stirred at the same temperature for one hour, 0.547 ml (7.49 mmol) of DMF is added thereto and then, allowed to stand and stirred until cooled down to room temperature and then, stirred at the room temperature for 12 hours. H$_2$O is used to separate and extract an organic layer, and the organic layer is separated and purified through column chromatography to obtain 1.88 g (6.37 mmol) of Compound 1-3B.

$^1$H NMR (300 mHz, CD$_2$Cl$_3$) 9.84 (s, 1H), 7.79 (s, 1H), 7.54 (d, 1H), 7.14 (d, 1H), 0.90 (s, 6H)

(3) Synthesis of Compound Represented by Chemical Formula 1-3

1.5 g (5.08 mmol) of Compound 1-3B and 0.99 g (5.08 mmol) of 1H-cyclopenta[b]naphthalene-1,3(2H)-dione are dissolved in 50 ml of a mixed solution of chloroform and ethanol in a volume ratio of 1:2 and then, refluxed and stirred for 12 hours and recrystallized by using 250 ml of a mixed solvent of chloroform and methanol (a volume ratio=2:3) to obtain 2.28 g (4.83 mmol) of a compound represented by Chemical Formula 1-3.

$^1$H NMR (300 mHz, CD$_2$Cl$_3$) 8.85 (s, 2H), 8.46 (s, 1H), 8.15 (d, 2H), 7.84 (s, 1H), 7.76 (dd, 2H), 7.54 (d, 1H), 7.14 (d, 1H), 0.90 (s, 6H)

Synthesis Example 4: Synthesis of Compound Represented by Chemical Formula 1-4

[Chemical Formula 1-4]

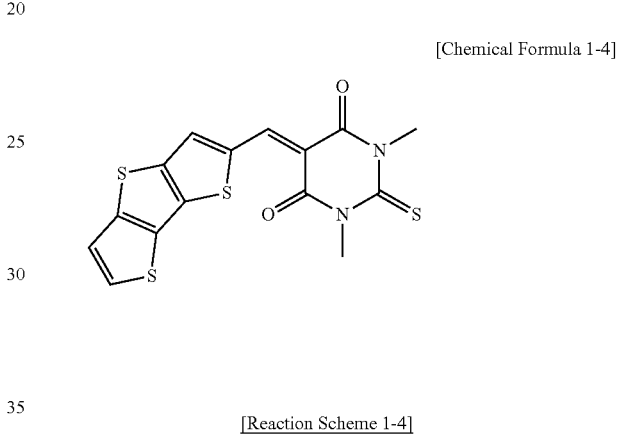

[Reaction Scheme 1-4]

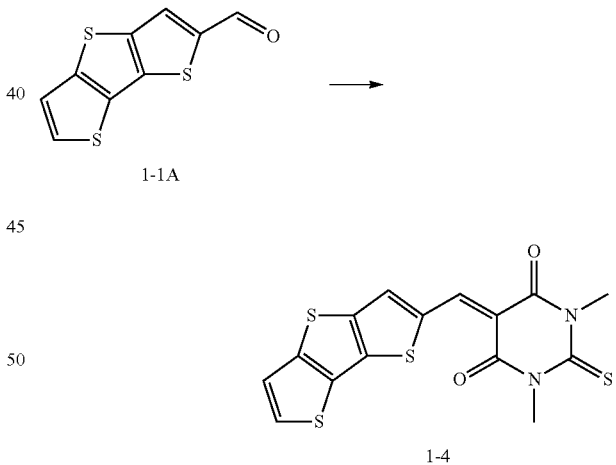

1.76 g (7.86 mmol) of Compound 1-1A synthesized in Synthesis Example 1 and 1.22 g (7.07 mmol) of 1,3-dimethyl-2-thiodihydropyrimidine-4,6(1H,5H)-dione are dissolved in 50 ml of a mixed solvent of chloroform and ethanol (a volume ratio=1:2) and then, refluxed and stirred for 12 hours and recrystallized by using chloroform methanol to obtain 1.84 g (4.87 mmol) of a compound represented by Chemical Formula 1-4.

$^1$H NMR (300 mHz, CD$_2$Cl$_3$) 8.19 (s, 1H), 8.03 (s, 1H), 7.33 (d, 1H), 7.12 (d, 1H), 3.55 (s, 6H),

Comparative Synthesis Example 1: Synthesis of Compound Represented by Chemical Formula 1-5

[Chemical Formula 1-5]

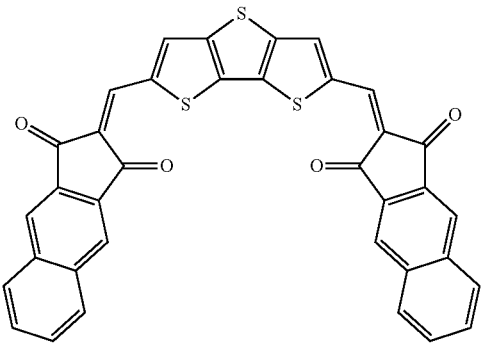

[Reaction Scheme 1-5]

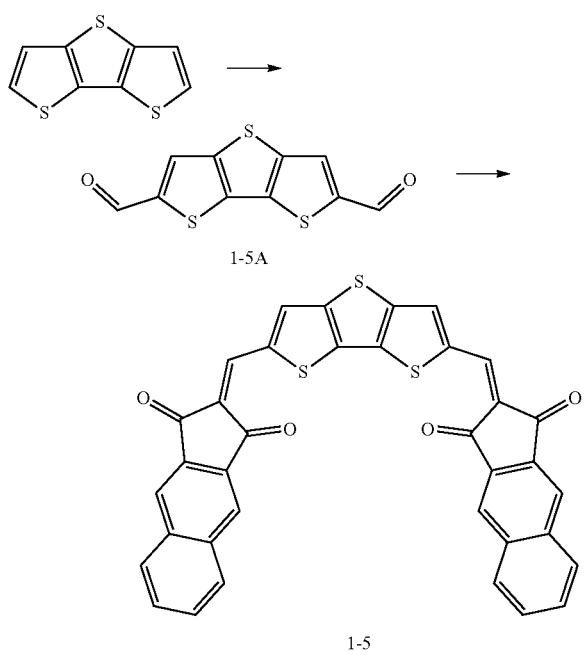

(1) Synthesis of Compound 1-5A 2.00 g (10.19 mmol) of 3,2-b:2',3'-d]thiophene(dithieno[3,2-b:2',3'-d]thiophene) is dissolved in 30 ml of tetrahydrofuran (THF) and then, cooled down to −78° C. and stirred for 10 minutes, and 9.78 ml (24.46 mmol) of normal butyllithium is drop by drop added thereto. After stirred at the same temperature for one hour, 3.14 ml (40.76 mmol) of dimethyl formamide (DMF) is added thereto and then, allowed to stand and stirred until cooled down to room temperature (24° C.), 10 ml of $H_2O$ is added thereto, and an organic layer is gathered therefrom and separated and purified through column chromatography to obtain 1.41 g (5.60 mmol) of Compound 1-5A (dithieno[3,2-b:2',3'-d]thiophene-2,6-dicarbaldehyde).

$^1$H NMR (300 mHz, $CD_2Cl_3$) 9.84 (s, 2H), 8.13 (s, 2H).

(2) Synthesis of Compound Represented by Chemical Formula 1-5

1.41 g (5.60 mmol) of Compound 1-5A and 3.31 g (16.97 mmol) of 1H-cyclopenta[b]naphthalene-1,3(2H)-dione are dissolved in 200 ml of a mixed solvent of chloroform and ethanol (a volume ratio=1:2) and then, refluxed and stirred for 12 hours and recrystallized with chloroform methanol to obtain 1.36 g (2.24 mmol) of a compound represented by Chemical Formula 1-5.

$^1$H NMR (300 mHz, $CD_2Cl_3$) 8.87 (s, 4H), 8.48 (s, 2H), 8.18 (s, 2H), 8.16 (d, 4H), 7.79 (dd, 4H).

Example 1: Manufacture of Photoelectric Device

ITO is deposited through sputtering on a glass substrate to form an about 150 nm-thick anode, and the ITO glass substrate is ultrasonic wave-cleaned under in acetone/isopropyl alcohol/pure water respectively for 15 minutes and then, UV ozone-cleaned. Subsequently, the compound of Synthesis Example 1 and C60 are codeposited in a volume ratio of 1:1 to form a 1000 nm-thick active layer, and Al is vacuum-deposited thereon to be 70 nm thick to manufacture a photoelectric device having a structure of ITO (150 nm)/active layer (1000 nm)/Al (70 nm).

Examples 2 to 4: Manufacture of Photoelectric Device

Photoelectric devices of Examples 2 to 4 are manufactured according to the same method as Example 1 except that the compounds of Synthesis Examples 2 to 4 are respectively used instead of the compound of Synthesis Example 1.

Evaluation 1: Light Absorption Characteristics of Compounds

Light absorption characteristics (a maximum absorption wavelength and a full width at half maximum (FWHM)) of the compounds of Synthesis Examples 1 to 3 depending on a wavelength are evaluated. Each compound of Synthesis Examples 1 to 3 (a P-type semiconductor compound) and C60 (an N-type semiconductor compound) are codeposited in a volume ratio of 1:1.2 to form thin films, and the light absorption characteristics of the thin films are evaluated by using Cary 5000 UV spectroscopy (Varian Medical Systems, Inc.) in an ultraviolet-visible ray (UV-Vis) region. The results are shown in Table 1.

In addition, HOMO of the compounds of Synthesis Examples 1 to 3 are measured by using an AC-3 photoelectron spectrophotometer (RIKEN KEIKI Co., Ltd.), and LUMO thereof is calculated by measuring a bandgap with Cary 5000 UV spectroscopy (Varian Medical Systems, Inc.) and using it. The results are shown in Table 1.

Reorganization energy and oscillator strength are measured by using a Gaussian 09 program in a DFT B3LYP/6-311G (d,p) level.

TABLE 1

| Compound | $\lambda_{max}$ (nm) | FWHM (nm) | HOMO (eV) | LUMO (eV) | Reorganization Energy (eV) | Oscillator Strength (a.u.) |
|---|---|---|---|---|---|---|
| Synthesis Example 1 | 525.00 | 113 | −6.03 | −3.11 | 0.252 | 1.47 |

TABLE 1-continued

| Compound | $\lambda_{max}$ (nm) | FWHM (nm) | HOMO (eV) | LUMO (eV) | Reorganization Energy (eV) | Oscillator Strength (a.u.) |
|---|---|---|---|---|---|---|
| Synthesis Example 2 | 535.25 | 114 | −5.95 | −3.13 | 0.268 | 1.42 |
| Synthesis Example 3 | 540.21 | 119 | −5.84 | −3.19 | 0.296 | 1.11 |

Referring to Table 1, the compounds of Synthesis Examples 1 to 3 have a maximum absorption wavelength in a green wavelength region and in addition, a low full width at half maximum (FWHM). Accordingly, the compounds of Synthesis Examples 1 to 3 have high wavelength selectivity in the green wavelength region. In addition, the energy levels (HOMO and LUMO) exhibit that the compounds of Synthesis Examples 1 to 3 may be appropriately used as a p-type semiconductor.

The compounds have low reorganization energy and thus are expected to exhibit excellent molecular stability and packing properties during the deposition process and in addition, have high oscillator strength and thus are expected to have a high absorption coefficient.

Evaluation 2: Planarity of Compound

The compounds of Synthesis Examples 1 and 2 are respectively calculated with respect to a molecular skeleton of an energetically-optimized structure through Density Functional Theory (DFT), and in the corresponding skeleton, a ratio (Z/X) of the shortest length (Z) relative to the longest length (X) is calculated to obtain an aspect ratio. The results are shown in Table 2. For comparison, the aspect ratios of the compounds of Structure 1 and Structure 2 are shown together in Table 2.

[Structure 1]

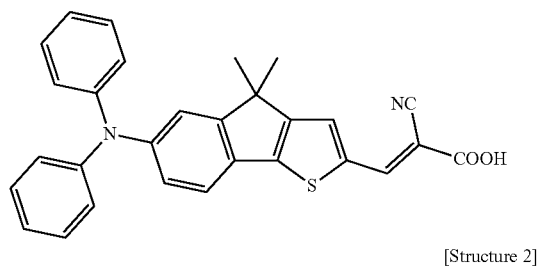

[Structure 2]

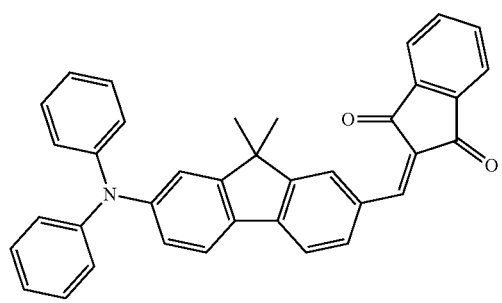

TABLE 2

| Compound | Aspect ratio (Z/X) |
|---|---|
| Synthesis Example 1 | 0.190 |
| Synthesis Example 2 | 0.201 |
| Structure 1 | 0.361 |
| Structure 2 | 0.314 |

Referring to Table 2, the compounds of Synthesis Examples 1 and 2 exhibit a low aspect ratio compared with compounds having structures 1 and 2. Accordingly, the compounds of Synthesis Examples 1 and 2 maintain flatness.

Evaluation 3: Thermal Stability of Compounds

In order to evaluate thermal stability of the compounds according to Synthesis Examples 1 to 3, a temperature ($Ts_{10}$, a deposition temperature) where 10 wt % thereof is sublimated at 10 Pa, and a temperature ($Ts_{50}$, a deposition temperature) where 50 wt % is sublimated at 10 Pa are measured. The deposition temperatures are measured in a thermal gravimetric analysis (TGA) method while increasing the temperature from room temperature to 500° C. The results are shown in Table 3.

TABLE 3

| | Tm (° C.) | $Ts_{10}$ (10 Wt %, 10 Pa) (° C.) | $Ts_{50}$ (50 wt %, 10 Pa) (° C.) | ΔT (Tm-Ts) (° C.) |
|---|---|---|---|---|
| Synthesis Example 1 | 339 | 256 | 386 | 83 |
| Synthesis Example 2 | 348 | 267 | 389 | 81 |
| Synthesis Example 3 | 292 | 219 | 245 | 73 |

When a compound has a lower melting point than a deposition temperature during the vacuum deposition, the compound may be decomposed and simultaneously gasified and thus fails in being formed into a film. Accordingly, the melting point of a compound may desirably be higher than the deposition temperature. Referring to Table 2, the melting points of the compounds according to the synthesis examples are greater than 73° C. than the deposition temperatures thereof. Accordingly, the compounds of Synthesis Examples 1 to 3 all exhibit a large difference between melting points and deposition temperatures and thus may advantageously secure process stability.

On the contrary, the compound of Comparative Synthesis Example 1 is all decomposed during the sublimation purification and thus not formed into a thin film.

Evaluation 4: Electrical Properties of Photoelectric Device

In order to evaluate charge mobility, TOF mobility is measured. The TOF mobility of the photoelectric devices of Examples 1 to 3 is measured by using PTI (Photon Technology International GL-3300, an $N_2$ laser, 337 nm) as a light source and a storage oscilloscope (1 GHz).

Remaining electrons are measured in a method of obtaining the number of remaining carriers per $\mu m^2$ by irradiating light with a LED light source (10 $\mu W/cm^2$, 530 nm) ($1^{st}$ frame) and then, integrating a remaining current from 3 $\mu s$ to 33 ms by time at 30 FPS ($2^{nd}$ frame).

The results are shown in Table 4.

TABLE 4

| Example | TOF mobility (cm²/V · sec) | Remaining electrons |
|---|---|---|
| Example 1 | 5.3 × 10⁻³ | 20 |
| Example 2 | 5.4 × 10⁻³ | 21 |
| Example 3 | 6.3 × 10⁻³ | 21 |

Referring to Table 4, the photoelectric devices of Example 1 to 3 respectively including Synthesis Examples 1 to 3 turn out to have excellent mobility and remaining electron characteristics.

While this disclosure has been described in connection with what is presently considered to be practical example embodiments, it is to be understood that inventive concepts are not limited to the disclosed embodiments. On the contrary, it is intended to cover various modifications and equivalent arrangements included within the spirit and scope of the appended claims.

<Description of Symbols>

| | |
|---|---|
| 10: first electrode | 20: second electrode |
| 30: active layer | 40, 45: charge auxiliary layer |
| 100, 200: photoelectric device | 300, 400, 500: organic CMOS image sensor |
| 310: semiconductor substrate | 70B, 72B: blue filter 70R, 72R: red filter |
| 70, 72: color filter layer | 85: through-hole |
| 60: lower insulation layer | 80: upper insulation layer |
| 50B, 50R: photo-sensing device | 55: charge storage |

What is claimed is:

1. A compound represented by Chemical Formula 1:

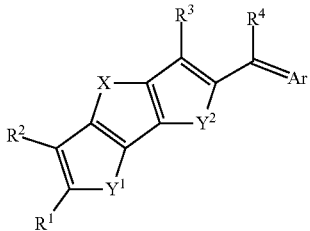

[Chemical Formula 1]

wherein, in Chemical Formula 1,
Ar is a substituted or unsubstituted C2 to C30 hydrocarbon cyclic group, a substituted or unsubstituted C6 to C30 heterocyclic group, or a fused ring thereof,
Ar has at least one functional group selected from C=O, C=S, C=Se, and C=Te,
X is O, S, Se, Te, S(=O), S(=O)$_2$, SiR$^a$R$^b$, GeR$^c$R$^d$, or CR$^e$R$^f$ (wherein R$^a$, R$^b$, R$^c$, R$^d$, R$^e$, and R$^f$ are independently hydrogen or a substituted or unsubstituted C1 to C10 alkyl group, and wherein R$^a$, R$^b$, R$^c$, R$^d$, R$^e$, and R$^f$ are independently present and R$^a$ and R$^b$, R$^c$ and R$^d$, or R$^e$ and R$^f$ are linked to each other to provide a spiro structure),
Y$^1$ and Y$^2$ are independently O, S, Se, or Te, and
R$^1$ to R$^4$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$, and R$^c$ are independently hydrogen or a substituted or unsubstituted C1 to C10 alkyl group), or a combination thereof, or
adjacent two groups of R$^1$ to R$^4$ are linked to each other to provide a substituted or unsubstituted C5 to C30 hydrocarbon cyclic group or a substituted or unsubstituted C2 to C30 heterocyclic group.

2. The compound of claim 1, wherein in Chemical Formula 1, Y$^1$ and Y$^2$ are the same or different.

3. The compound of claim 1, wherein in Chemical Formula 1, X is the same as or different from Y$^1$ and Y$^2$.

4. The compound of claim 1, wherein
in Chemical Formula 1,
X is one of S, Se, and Te, and
Y$^1$ and Y$^2$ are independently one of S, Se, and Te.

5. The compound of claim 1, wherein
in Chemical Formula 1, X is one of SiR$^a$R$^b$, GeR$^c$R$^d$, and CR$^e$R$^f$,
Y$^1$ and Y$^2$ are independently one of O, S, Se, and Te.

6. The compound of claim 1, wherein Ar is represented by Chemical Formula 3:

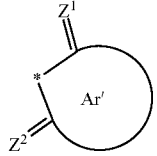

[Chemical Formula 3]

wherein, in Chemical Formula 3,
Ar' is a substituted or unsubstituted C6 to C30 aryl group or a substituted or unsubstituted C3 to C30 heteroaryl group,
Z$^1$ is O, S, Se, or Te, and
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, provided that when Z$^2$ is CR$^a$R$^b$, at least one of R$^a$ and R$^b$ is a cyano group or a cyano-containing group.

7. The compound of claim 1, wherein in Chemical Formula 1, Ar is a cyclic group represented by one of Chemical Formulae 4A to 4F:

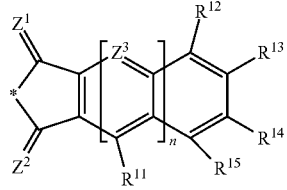

[Chemical Formula 4A]

wherein, in Chemical Formula 4A,
Z$^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen, deuterium, or a substituted or unsubstituted C1 to C10 alkyl group), $R^{11}$, $R^{12}$, $R^{13}$, $R^{14}$, and $R^{15}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{11}$, $R^{12}$, $R^{13}$, $R^{14}$, and $R^{15}$ are independently present or at least one of $R^{12}$ and $R^{13}$ and $R^{14}$ and $R^{15}$ is linked with each other to provide a fused aromatic ring, n is 0 or 1, and

* is a linking position,

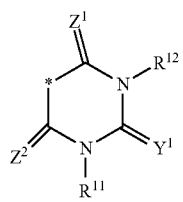

[Chemical Formula 4B]

wherein, in Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$ (wherein $R^a$ is hydrogen, a cyano group (—CN), or a C1 to C10 alkyl group), $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking position,

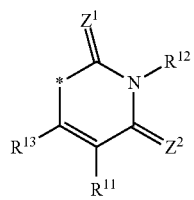

[Chemical Formula 4C]

wherein, in Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position,

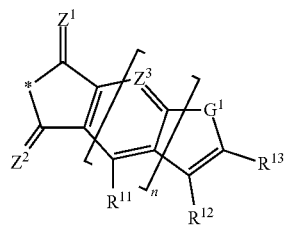

[Chemical Formula 4D]

wherein, in Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently different and are linked with each other to provide a fused aromatic ring, n is 0 or 1, and

* is a linking position,

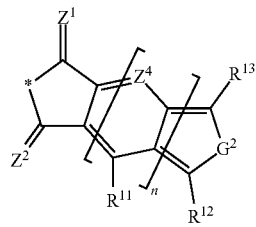

[Chemical Formula 4E]

wherein, in Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^4$ is N or $CR^c$ (wherein $R^c$ is hydrogen or a substituted or unsubstituted C1 to C10 alkyl group), $G^2$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group, $R^{11}$, $R^{12}$, and $R^{13}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking position,

[Chemical Formula 4F]

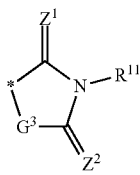

wherein, in Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are independently hydrogen, a halogen, a substituted or unsubstituted C1 to C10 alkyl group, or a substituted or unsubstituted C6 to C10 aryl group.

8. The compound of claim 1, wherein
the compound represented by Chemical Formula 1 has an aspect ratio (Z/X) in a range of less than or equal to about 0.30, and
the aspect ratio is obtained by dividing a shortest length (Z) of the compound by a longest length (X) of the compound.

9. The compound of claim 1, wherein the compound has a maximum absorption wavelength ($\lambda_{max}$) in a wavelength range of greater than or equal to about 500 nm and less than or equal to about 580 nm.

10. The compound of claim 1, wherein the compound exhibits a light absorption curve having a full width at half maximum (FWHM) of about 50 nm to about 120 nm.

11. The compound of claim 1, wherein a difference between a melting point of the compound and a temperature at which 10 wt % of an initial weight is lost (deposition temperature) is greater than or equal to about 10° C.

12. A photoelectric device, comprising:
a first electrode and a second electrode facing each other, and
an active layer interposed between the first electrode and the second electrode,
wherein the active layer comprises the compound of claim 1.

13. An image sensor comprising:
the photoelectric device of claim 12.

14. The image sensor of claim 13, further comprising:
a semiconductor substrate integrated with a plurality of first photo-sensing devices configured to sense light in a blue wavelength region and a plurality of second photo-sensing devices configured to sense light in a red wavelength region, wherein
the photoelectric device is on the semiconductor substrate and configured to selectively sense light in a green wavelength region.

15. The image sensor of claim 14, further comprising: a color filter layer comprising a blue filter configured to selectively transmit light in a blue wavelength region and a red filter configured to selectively transmit light in a red wavelength region.

16. The image sensor of claim 14, wherein the first photo-sensing device and the second photo-sensing device are stacked in a vertical direction in the semiconductor substrate.

17. The image sensor of claim 13, further comprising:
a blue photoelectric device configured to selectively absorb light in a blue wavelength region; and
a red photoelectric device configured to selectively absorb light in a red wavelength region, wherein
the photoelectric device is a green photoelectric device and an organic photoelectric device,
the green photoelectric device, the blue photoelectric device, and the red photoelectric device are stacked.

18. An electronic device comprising:
the image sensor of claim 13.

* * * * *